United States Patent [19]
Ohta et al.

[11] Patent Number: 5,338,378
[45] Date of Patent: Aug. 16, 1994

[54] DENTAL GOLD ALLOY WITH AGE-HARDENABILITY AT INTRAORAL TEMPERATURE

[75] Inventors: Michio Ohta; Shigeki Matsuya, Fukuoka; Takanobu Shiraishi, Kaga; Masaharu Nakagawa, Fukuoka, all of Japan

[73] Assignee: Kyushu University, Fukuoka, Japan

[21] Appl. No.: 51,299

[22] Filed: Apr. 23, 1993

[30] Foreign Application Priority Data

Sep. 29, 1992 [JP] Japan .................................. 4-260075

[51] Int. Cl.$^5$ ................................................ C22C 5/02
[52] U.S. Cl. ..................................... 148/405; 420/507; 148/678; 433/207
[58] Field of Search ................ 420/507; 148/405, 430, 148/538, 539, 559, 567, 574, 577, 678; 433/207

[56] References Cited

U.S. PATENT DOCUMENTS

3,861,455 1/1975 Ingersoll .............................. 164/122

FOREIGN PATENT DOCUMENTS

2303519 1/1972 Fed. Rep. of Germany ...... 420/507
257891 8/1927 United Kingdom ................ 420/507

OTHER PUBLICATIONS

Ohta, M., et al., "Development of Dental Gold Alloys With Age-Hardenability At Intraoral Temperature", Fourth World Biomaterials Congress, Berlin, FRG, Apr. 24-28, 1992, p. 378.
*The Science News*, vol. 4, p. 2412, (see graph in lower left), Jun. 5, 1992.
International Standard, ISO 1562-1976(E), "Dental Casting Gold Alloys", pp. 186–184.
"American Dental Associationspecification No. 5 for dental casting gold alloy", American Dental Association Specificaiton No. 5, Apr. 1965, pp. 184–186.

*Primary Examiner*—Richard O. Dean
*Assistant Examiner*—Sean Vincent
*Attorney, Agent, or Firm*—Spencer, Frank & Schneider

[57] ABSTRACT

A dental gold alloy which is soft enough for adjustment of a patient's occlusal condition, which is age-hardenable with passage of time at temperatures encountered within a patient's oral cavity, and which has a single phase structure which imparts improved corrosion resistance, the dental gold alloy consisting essentially of 82–67% by a weight of gold; 18–33% by weight of copper; and 2–8 at % of an age-hardening accelerator which is at least one metal selected from the group consisting of gallium, aluminum and zinc, wherein the dental gold alloy has been subjected to a solution treatment by heating at 670–700° C. and quenching into water.

4 Claims, 6 Drawing Sheets

FIG_3
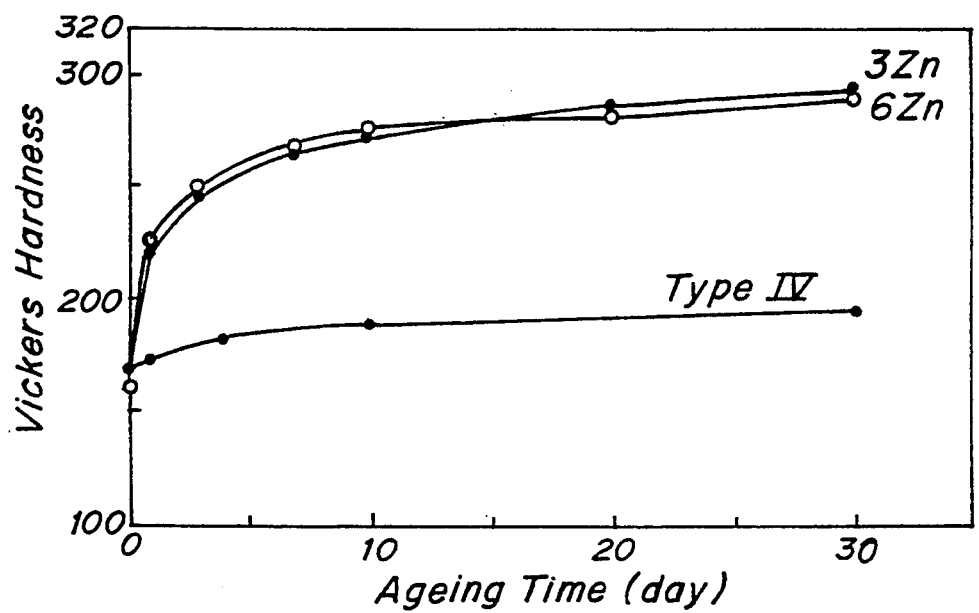
FIG_4
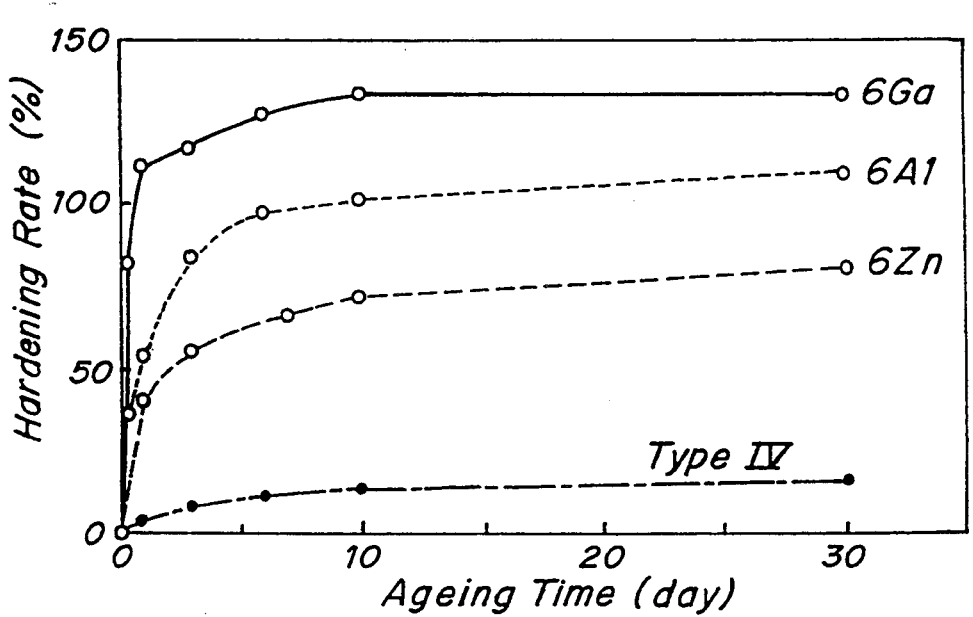

FIG_5
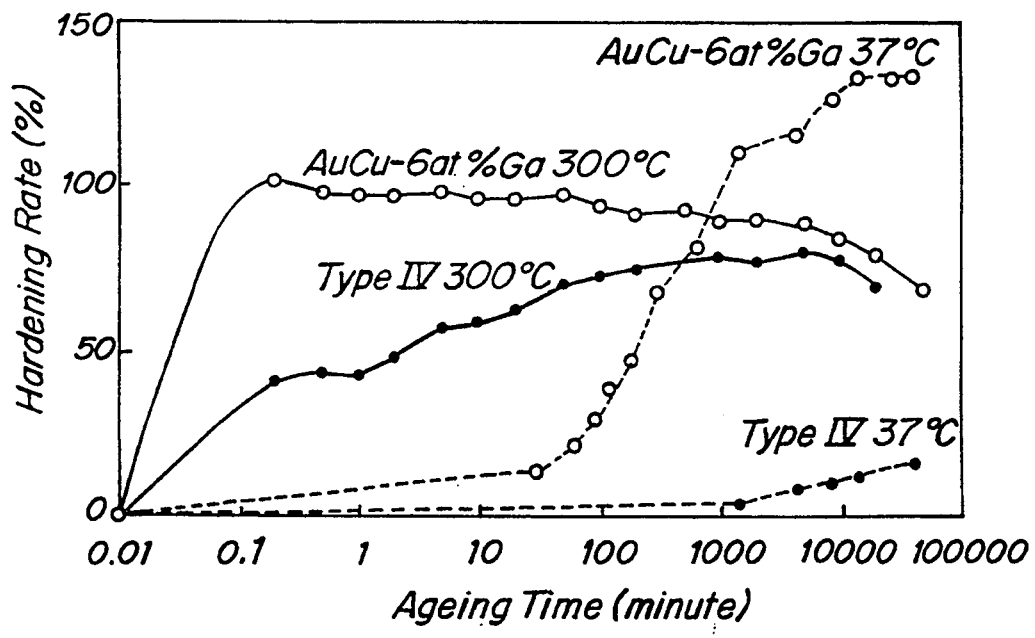
FIG_6
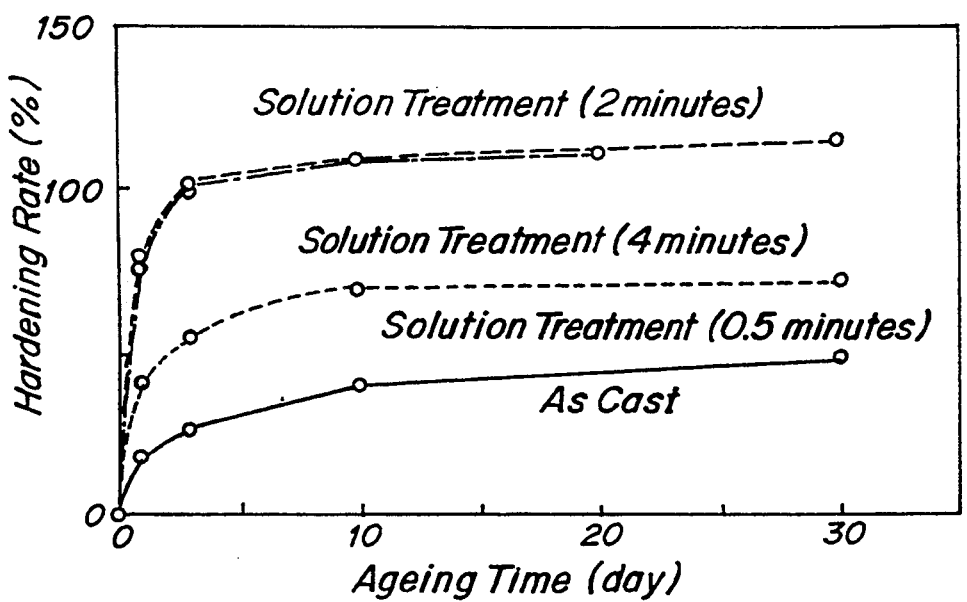

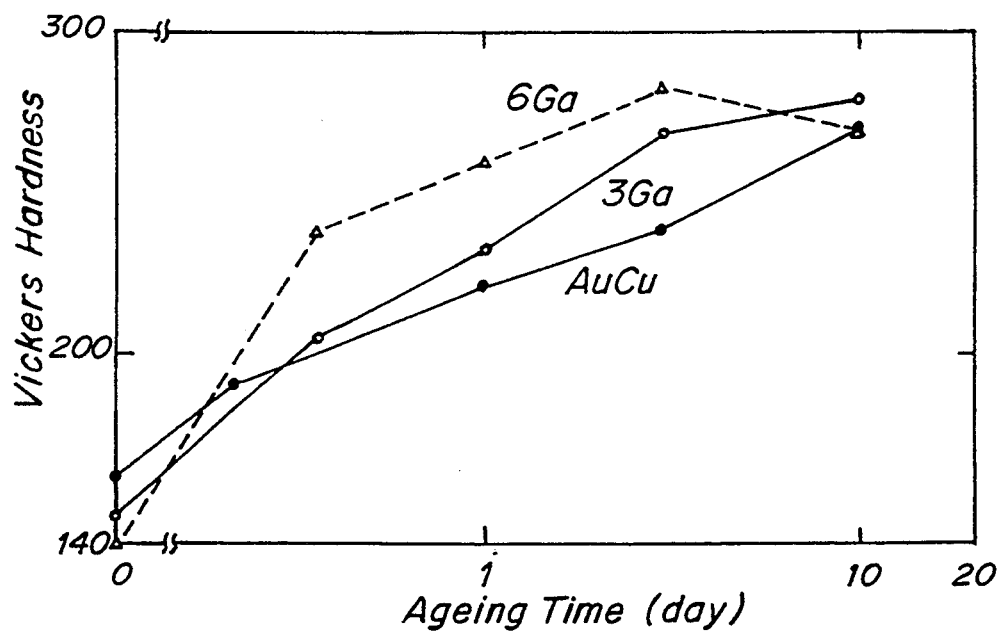
FIG_10
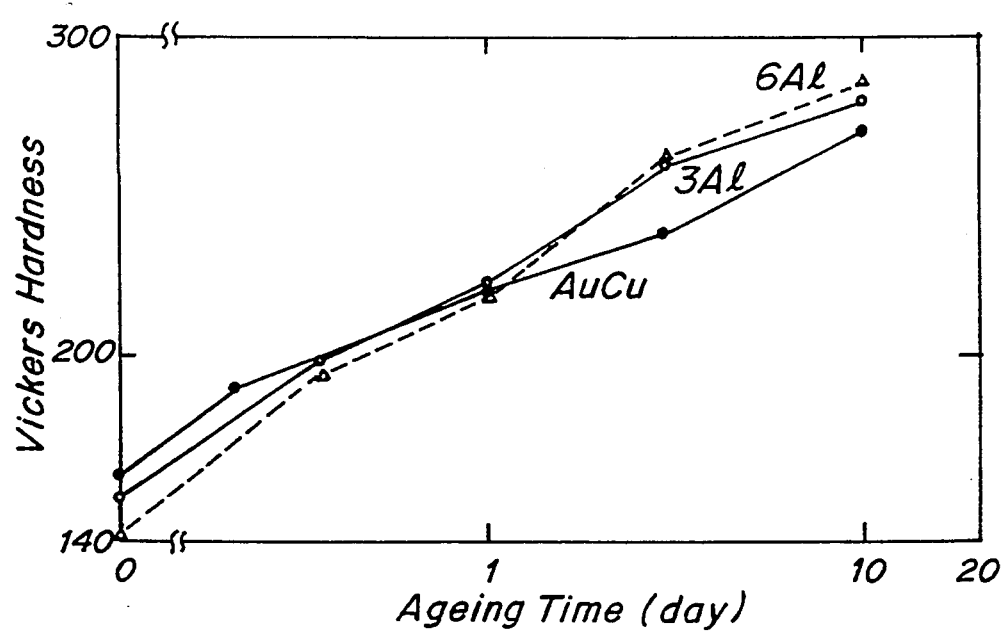
FIG_11

DENTAL GOLD ALLOY WITH AGE-HARDENABILITY AT INTRAORAL TEMPERATURE

BACKGROUND OF THE INVENTION

1. Field of Invention

The present invention relates to a dental gold alloy having a corrosion-resistant single phase structure and being age-hardenable at a temperature of about 37° C. within the oral cavity. The industrially applicable field of the alloy of the present invention covers at least one alloy selected from a dental casting gold alloy, a dental casting gold alloy corresponding to ADA Specification Type III and Type IV, a wrought alloy etc.

2. Related Art Statement

It has hitherto been required to use a dental restorative alloy in the as-cast state to fit into a patient's occlusal condition with a tolerance on the order of several ten microns. Even if the cast is manufactured by precise casting, trial fitting and adjustment are necessary. Therefore, manufacturers specify a softening heat treatment (i.e., solution treatment, such as heating at 700° C. for 10 minutes and thereafter quenching in water) and a hardening heat treatment (i.e., aging treatment, such as heating in a furnace at 450° C. and thereafter slow cooling to 250° C.) for obtaining an alloy which is softened at the time of adjustment and hardened enough to sufficiently withstand against deformation by biting force.

In actual clinical treatment, however, such a complicated heat treatment is hardly carried out. In practice, therefore, an alloy composition is defined to have sufficient strength in the as-cast condition and as a result, a commercial alloy becomes a quaternary or pentanary alloy, and its structure becomes complicated by coexisting multiphases. Such structure is seriously disadvantageous in view of the most important corrosion resistance as a desired property of dental alloy.

SUMMARY OF THE INVENTION

The present invention is directed to obviating the above shortcoming, and it relates to a dental gold alloy age-hardenable at the intraoral temperature. The alloy consists essentially of 60–40 at % (82–67 wt %) of gold, 40–60 at % (18–33 wt %) of copper and 2–8 at % of at least one element selected from the group consisting essentially of gallium, aluminum and zinc to accelerate age-hardening. The alloy is solution treated by heating at 650–700° C. and thereafter quenching into water.

An object of the present invention is to develop a dental gold alloy having a corrosion-resistant single phase structure and being age-hardenable at intraoral temperature. If age-hardenability at a low temperature such as the intraoral temperature is provided in a dental restorative alloy, the alloy is soft enough for the adjustment of the occlusal condition and becomes hard enough with the passage of time, without any hardening heat treatment, as the occlusal condition fits the patient.

The alloy of the present invention relates to a ternary or multicomponent system gold alloy consisting essentially of 67–82 wt % gold and 18–33 wt % copper and 2–8 at % in total of at least one element selected from the group consisting essentially of 1–4 wt % gallium, 0.4–2 wt % aluminum and 1–5 wt % zinc as the element to accelerate age-hardening.

Age-hardening of a dental gold alloy is attributed to the formation of a gold-copper ordered lattice (AuCuI-type ordered lattice). Since the age-hardening temperature of a gold alloy is considerably high, the following two factors are important to harden the gold alloy by aging at a low temperature; nuclei of the ordered lattice must already exist in the solution treated alloy, and diffusion rate of atoms in the crystal must be sufficiently large even at a low temperature. Accordingly, age-hardening tests were carried out on the alloys consisting of equiatomic Au-Cu (75 wt % Au-25 wt % Cu) and additives for acceleration of age-hardening. As a result, a dental gold alloy with age-hardenability at the intraoral temperature has been found and development of an alloy of the present invention has succeeded.

BRIEF DESCRIPTION OF THE DRAWINGS

FIG. 3 shows age-hardening curves of gold-copper-zinc alloys (3Zn:74.5 wt % Au-24.0 wt % Cu-1.5 wt % Zn, 6Zn:73.3 wt % Au-23.6 wt % Cu-3.1 wt % Zn) of the present invention and of a commercial Type IV gold alloy at 37° C.;

FIG. 4 shows the change in hardening rate with aging time at 37° C. of gold-copper alloys of the present invention consisting essentially of 6 at % of gallium, aluminum and zinc with that of a commercial Type IV gold alloy;

FIG. 5 shows age-hardening curves of a gold-copper alloy consisting essentially of 6 at % gallium of the present invention and of a commercial Type IV gold alloy at 37° C. and at 300° C., respectively;

FIG. 6 shows the relationship between age-hardening rate and solution treatment time for a cast gold alloy consisting essentially of 6 at % gallium of the present invention;

FIG. 10 shows the relationship between Vickers hardness and aging time for the AuCu alloy and for Ga-added AuCu alloys of the present invention; and FIG. 11 shows the relationship between Vickers hardness and aging time for a AuCu alloy and for Al-added AuCu alloys of the present invention.

DESCRIPTION OF THE PREFERRED EMBODIMENT

The present invention relates to an alloy having a new function, so that the most important conditions lie in constituent elements, a chemical composition and a heat treatment method of the alloy. The essentials thereof are shown below.

(1) A gold-copper alloy at an equiatomic ratio (75 wt % Au-25 wt % Cu) is chosen as a basis and the composition should be within a range where a AuCuI-type ordered lattice is formed. It is considered that the age-hardening rate is lowered as the gold-copper ratio of the alloy deviates from the equiatomic one, so that a composition of gold and copper is within a range of 60–40 and 40–60 at % (i.e., 82 wt % Au-18 wt % Cu~67 wt % Au-33 wt % Cu), respectively.

(2) As the element to accelerate age-hardening, at least one element selected from the group consisting essentially of 1–4 wt % gallium, 0.4–2 wt % aluminum and 1–5wt % zinc are added 2–8 at % in total.

(3) A total amount of gallium, aluminum and zinc added is 2 at % at least and 8 at % at most. Minimum amount is the lowest amount at which effect of addition becomes perceptible. At the maximum addition, the difference in the effect of addition is scarcely distinguished and, moreover, further addition lowers the corrosion resistance of the alloy by precipitating a second phase.

(4) Solution treatment is carried out by heating the alloy in a furnace at a temperature lower than 700° C. (i.e., 650–700° C.) for 2–3 minutes and thereafter quenching it into water.

(5) Since the alloy of the present invention becomes hard by leaving it at room temperature, it is necessary to adjust the occlusal condition of the patient within 3–4 hours after solution treatment and to set the restoration onto the teeth of the patient. If the alloy is hardened by leaving it at room temperature for a long period of time, it is preferable to apply the solution treatment again.

(6) In case that an alloy should be kept in the soft condition for a long period of time after solution treatment, the alloy should be kept in a refrigerator or in a freezer.

It was found from the result of experiments that gallium (Ga), aluminum (Al) and zinc (Zn) are effective as the element to accelerate ordering of the AuCu alloy. The compositions of gold and copper should be in the region in the Au-Cu binary phase diagram, where AuCuI-type ordered lattice is formed. Accordingly, experiments were conducted using alloys having compositions of 60–40 at % Au and 40–60 at % Cu. The amounts of gallium, aluminum and zinc added were limited into the range of 2–8 at % to obtain a single phase structure.

Figure 1:
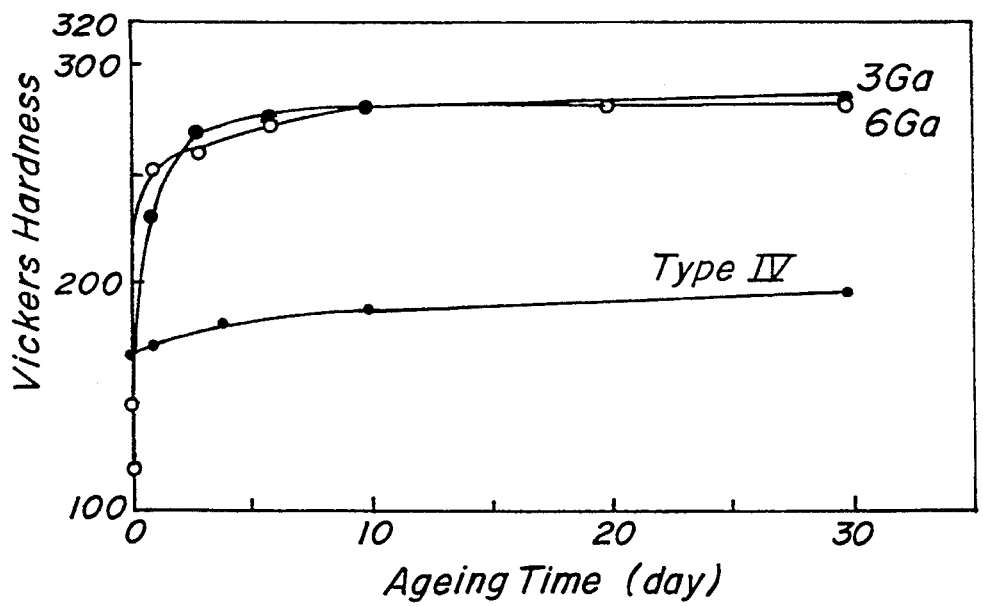
FIG. 1 shows age-hardening curves of gold-copper-gallium alloys (3Ga:74.4 wt % Au-24.0 wt % Cu-1.6 wt % Ga, 6Ga:73.1 wt % Au-23.6 wt % Cu-3.3 wt % Ga) of the present invention and of a commercial Type IV gold alloy (76 wt % Au, Pt, Pd-8 wt % Ag-16 wt % Cu) at 37° C.
Figure 2:
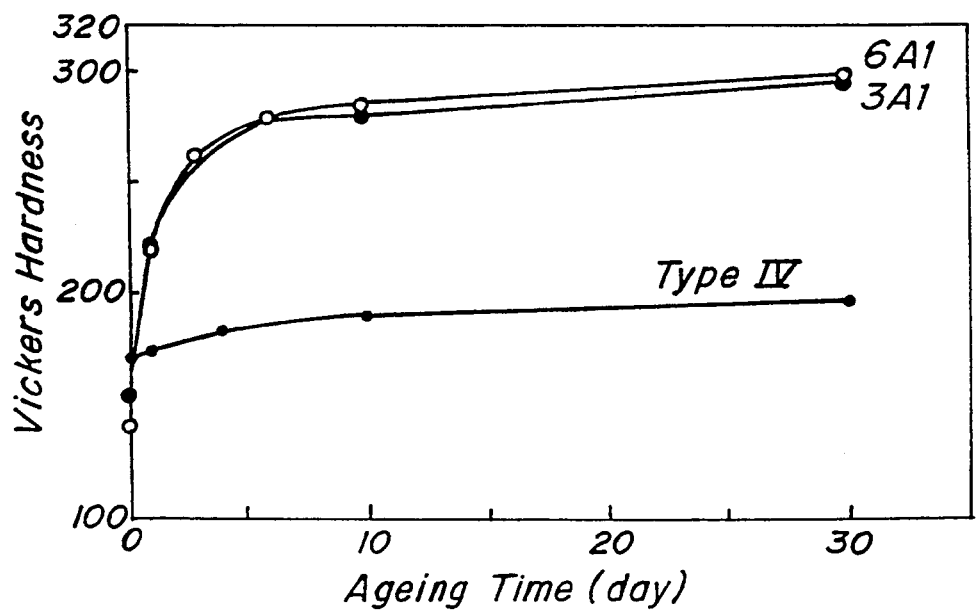
FIG. 2 shows age-hardening curves of gold-copper-aluminum alloys (3Al:75.1 wt % Au-24.3 wt % Cu-0.6 wt % Al, 6Al: 74.6 wt % Au-24.1 wt % Cu-1.3 wt % Al) of the present invention and of a commercial Type IV gold alloy at 37° C.

In FIGS. 1 through 3, age-hardening curves of Au-Cu-Ga (FIG. 1), Au-Cu-Al (FIG. 2) and Au-Cu-Zn (FIG. 3) alloys are shown, respectively, with that of a commercial Type IV gold alloy. These alloys were solution treated at 650° C. for 30 minutes followed by quenching into water, and then aged at 37° C. In FIG. 4, age-hardening rates at 37° C. of alloys consisting essentially of 6 at % Ga, 6 at % Al and 6 at % Zn are shown with that of a commercial Type IV gold alloy. The hardening rate is expressed as the ratio of the increment of hardness to the initial hardness. It is clear from FIGS. 1 through 4 that every alloy containing 3 to 6 at % of Ga, Al or Zn has high age-hardening rates at low temperature and that a commercial alloy has a low hardening rate. It is also clear from FIG. 4 that hardness values of these alloys increase to from 1.7 to 2.3 times the initial value in ten days after setting them into an oral cavity. The hardness values of these alloys at solution treated (Hv=120–150) and age-hardened states (Hv=280–300) are in the range the those of ADA Specification for Type III and Type IV casting gold alloys.

Heat treatment of the following methods are commonly applied to a dental gold alloy. The solution treatment, so-called softening treatment, is carried out by keeping the alloy at 700–800° C. for 5–10 minutes and then quenching it into water. For the aging treatment, so-called hardening treatment, either one of the following methods is applied.

(1) After the solution treatment, an alloy is kept at 350–400° C. for 10–15 minutes and then cooled.

(2) After the solution treatment, an alloy is kept at 450° C. for 5–10 minutes and slowly cooled to 250° C. in the furnace, then air-cooled.

In the present invention, a solution treatment is indispensable for hardening an alloy by a post aging treatment. By keeping an alloy at a high temperature for a period and quenching it into water, excess vacancies are introduced in the alloy at room temperature. These vacancies help the diffusion of atoms at the post aging treatment, resulting in the structural change and the hardening of the alloy. Accordingly, solution treatment is also essential for the alloy of the present invention. However, as shown in FIG. 5, the alloy of the present invention does not require any complicated aging treatment. This is the most important and characteristic feature of the present invention. FIG. 5 shows age-hardening rates of AuCu-6at % Ga alloy and a commercial Type IV gold alloy aged at 300° C. and 37° C. It is obvious from FIG. 5 that aging treatment at a high temperature, such as 300° C., is necessary for hardening a commercial alloy, but the AuCu alloy consisting of 6 at % Ga of the present invention shows sufficient age-hardenability at 37° C.

FIG. 6 shows change in the age-hardening rate at 37° C. of cast AuCu-6 at % Ga alloy with solution treatment time. Solution treatment was carried out at 680° C. for 0.5 to 4 minutes. The alloy does not show sufficient hardening at the as-cast state at 37° C., but the solution treatment for only 2 minutes provides enough age-hardenability.

Generally, in casting a gold alloy, the cast mold is heated at 700° C. in an oven to eliminate the wax completely and expand the mold thermally. The temperature of the oven is still kept at about 700° C. just after the casting is completed. Therefore, the solution treatment of the cast can be carried out by putting it in the oven for about 2 minutes and quenching it into water. Such a process does not require a precisely temperature-controlled furnace for the solution treatment, and is applicable in a dental laboratory without feeling troublesome.

Figure 7:
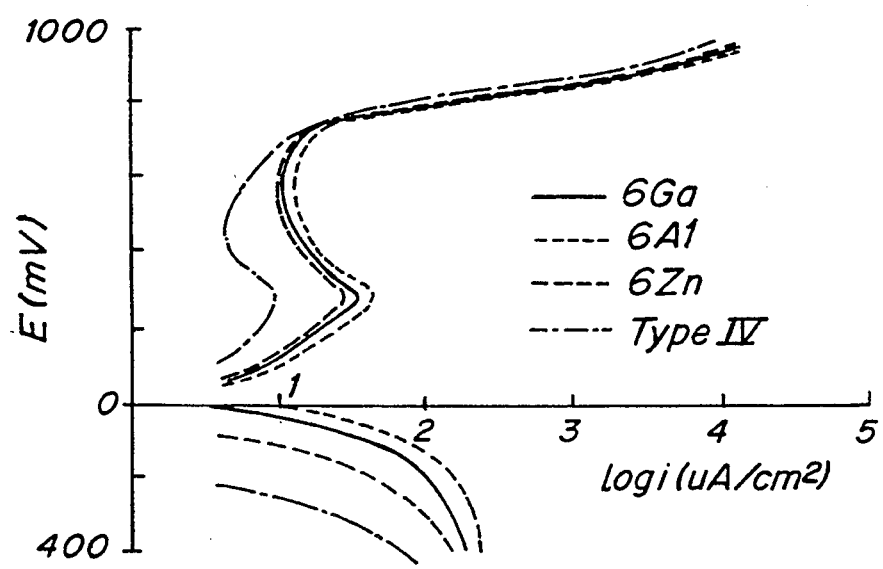
FIG. 7 shows potentiodynamic polarization curves of 6 at % gallium-gold-copper alloy, 6 at % aluminum-gold-copper alloy, 6 at % zinc-gold-copper alloy of the present invention and a commercial Type IV gold alloy in 1% saline solution.

FIG. 7 shows anodic potentiodynamic polarization curves of a 6 at % Ga alloy, a 6 at % Al alloy, and a 6 at % Zn alloy of the present invention, and of a commercial gold alloy in a 1% saline solution. Although every alloy of the present invention contains as much as about 24 wt % of copper, it was confirmed that all of these alloys show substantially the same corrosion resistance as that of a commercial alloy. This is attributed to the single phase structure of these alloys.

EXAMPLE 1

Age-hardening of a dental gold alloy is attributed to the formation of an ordered lattice in the Au-Cu system. In the present invention, therefore, a Au-Cu alloy of a stoichiometric composition of equiatomic ratio was chosen as a basic alloy, and alloys containing various additives were prepared and their low temperature age-hardenability was examined. In the equiatomic alloy, some amount of long-range ordering is accomplished during quenching, and further ordering is attained by short-range diffusion of atoms. The ease of nucleation of a long-range ordered lattice is closely related to the electron/atom ratio of the alloy, and the diffusion coefficient in a metal is related to the melting point of the metal. Therefore, in selecting the additive elements, both the melting point and the electron/atom ratio were taken into account. Table 1 shows chemical compositions of alloys used in the present invention.

TABLE 1

| | Chemical Composition of Alloy (at %) | | | | | |
|---|---|---|---|---|---|---|
| | Au | Cu | Pd | Ni | Ga | Al |
| AuCu | 50.0 | 50.0 | — | — | — | — |
| 3Pd | 48.5 | 48.5 | 3.0 | — | — | — |
| 6Pd | 47.0 | 47.0 | 6.0 | — | — | — |
| 3Ni | 48.5 | 48.5 | — | 3.0 | — | — |
| 6Ni | 47.0 | 47.0 | — | 6.0 | — | — |
| 3Ga | 48.5 | 48.5 | — | — | 3.0 | — |
| 6Ga | 47.0 | 47.0 | — | — | 6.0 | — |
| 3Al | 48.5 | 48.5 | — | — | — | 3.0 |
| 6Al | 47.0 | 47.0 | — | — | — | 6.0 |

The melting points of Pd and Ni are high and their electron/atom ratios are zero. On the other hand, the melting points of Ga and Al are low and their electron/atom ratios are larger than one. Maximum amount of addition of these elements was limited to 6 at % to form a single phase structure which is recommended from the standpoint of corrosion resistance. Alloys were prepared from 99.99% pure metals in evacuated quartz ampullae using a high frequency induction furnace. They were homogenized by cold-working, heating at 650° C. for 30 minutes and then quenching into iced brine. These specimens were kept at 37° C. in a dry oven for aging treatment. Micro Vickers hardness was measured just after quenching (i.e., after solution treatment), and after aging at 37° C. for 5 hours (or 8 hours), 1, 3 and 10 days. The results are shown in Table 2 and in FIG. 8.

TABLE 2

Figure 8:
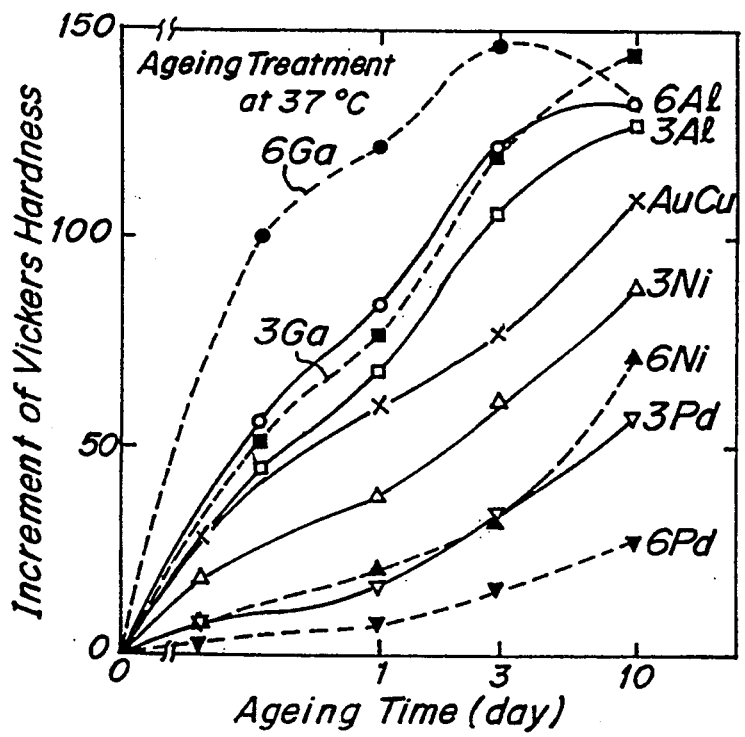
FIG. 8 shows increment of Vickers hardness with aging time of AuCu alloys consisting of Ga, Al, Ni or Pd.

| Specimen | | Ageing time (day) | | | | | | Symbol in FIG. 8 |
|---|---|---|---|---|---|---|---|---|
| | | 0 | 0.21 | 0.35 | 1 | 3 | 10 | |
| 3Ga | Hv | 148.2 | — | 203.8 | 232.2 | 269.7 | 280.4 | ○ |
| | ΔH | 0 | — | 55.6 | 84.0 | 121.5 | 132.2 | |
| 6Ga | Hv | 137.8 | — | 237.6 | 259.8 | 283.7 | 271.0 | ● |
| | ΔH | 0 | — | 99.8 | 122.0 | 145.9 | 133.2 | |
| 3Al | Hv | 154.1 | — | 198.5 | 222.1 | 260.2 | 281.3 | □ |
| | ΔH | 0 | — | 44.4 | 68.0 | 106.1 | 127.2 | |
| 6Al | Hv | 142.5 | — | 194.0 | 219.3 | 262.3 | 286.9 | ■ |
| | ΔH | 0 | — | 51.5 | 76.8 | 119.8 | 144.4 | |
| AuCu | Hv | 161.0 | 189.1 | — | 219.9 | 237.7 | 270.6 | x |
| | ΔH | 0 | 28.1 | — | 58.9 | 76.7 | 109.6 | |
| 3Ni | Hv | 172.4 | 190.4 | — | 210.6 | 232.7 | 260.6 | △ |
| | ΔH | 0 | 18.0 | — | 38.2 | 60.3 | 88.2 | |
| 6Ni | Hv | 175.3 | 183.1 | — | 195.4 | 207.9 | 247.6 | ▲ |
| | ΔH | 0 | 7.8 | — | 20.1 | 32.6 | 72.3 | |
| 3Pd | Hv | 167.5 | 175.0 | — | 183.8 | 201.0 | 224.5 | ▽ |
| | ΔH | 0 | 7.5 | — | 16.3 | 33.5 | 57.0 | |
| 6Pd | Hv | 168.5 | 171.8 | — | 175.9 | 184.3 | 195.5 | ▼ |
| | ΔH | 0 | 3.3 | — | 7.4 | 15.8 | 27.0 | |

ΔH is an increment of hardness (i.e., a difference from the hardness at ageing time equal to zero) and is plotted in FIG. 8 as a coordinate.

FIG. 8 is a graph of increment of Vickers and aging time for the AuCu alloys consisting of 3 and 6 at % Ga, Al, Ni and Pd. The Vickers hardness numbers of alloys after solution treatment were within a range from 140 (6Ga) to 175 (6Ni). Results obtained are shown in Table 2 and are summarized as follows.

(1) The equiatomic AuCu alloy has age-hardenability at low temperature.

(2) The addition of Ga or Al promotes the low-temperature age-hardening. Hardening rates of the alloys containing these elements increase with increasing amount of addition.

(3) Pd and Ni obstruct the development of ordering. Hardening rates of the alloys containing these elements decrease with increasing amount of addition.

In conclusion, a usefulness or serviceability of a dental gold alloy with age-hardenability at intraoral temperature was ascertained.

EXAMPLE 2

In order to compare the age-hardenability of alloys of the present invention with that of a commercial gold alloy, AuCu alloys consisting of 6 at % Ga or 6 at % Al were prepared in the same manner as in Example 1. The results of the experiment are shown in Table 3 and in FIGS. 9–11.

TABLE 3

Figure 9:
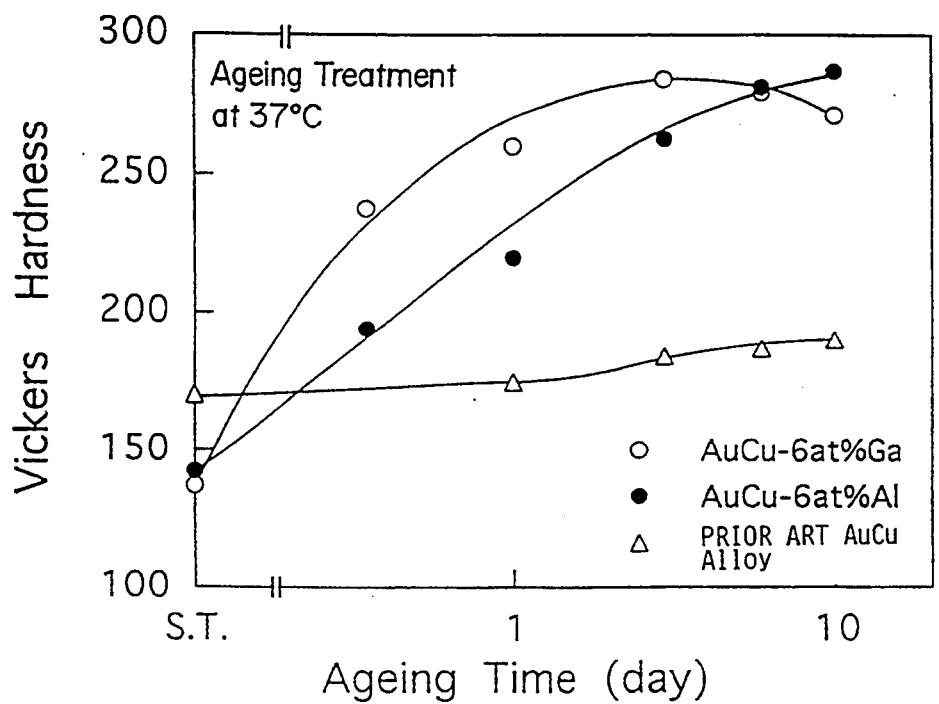
FIG. 9 shows the relationship between Vickers hardness and aging time for Ga- or Al-containing AuCu alloys of the present invention and for a commercial gold alloy.

| Specimen | Ageing time (day) | | | | | | Symbol in FIG. 9 |
|---|---|---|---|---|---|---|---|
| | 0 | 0.35 | 1 | 3 | 6 | 10 | |
| 6Ga | 137.8 | 237.6 | 259.8 | 283.7 | 279.3 | 271.0 | ○ |
| 6Al | 142.5 | 194.0 | 219.3 | 262.3 | 281.1 | 286.9 | ● |
| Commercial Alloy | 169.8 | — | 174.1 | 183.6 | 186.3 | 189.7 | △ |

It was confirmed from the above mentioned results of the experiments that the alloys of the present invention are extremely effective against attrition as dental restorative alloys.

Since the alloy of the present invention is basically a gold-copper alloy which consists of 40–60 at % Au, that is, 82–67 wt % Au and 18–33 wt % Cu, an ordered lattice is easily formed. As the accelerating element for age-hardening, at least one of 1–4 wt % Ga, 0.4–2 wt % Al and 1–5 wt % Zn is added by 2–8 at % in total. Although heat treatment at comparatively high temperature, such as 300° C., is required to harden a conventional gold alloy, the alloy of the present invention can be hardened at 37° C. which is the intraoral temperature. The amount of hardening at intraoral temperature is 20 to 50 times larger than that of a conventional gold alloy and the Vickers hardness number increases to 300–320, indicating sufficient hardening in the oral cavity. Thus, the alloy of the present invention is extremely useful as a dental gold alloy.

The alloy of the present invention is based on a gold-copper alloy and contains a large amount of gold. Therefore, it shows sufficient corrosion resistance when it is used in the oral cavity. Even if this base alloy is developed to ternary or multicomponent alloy by adding gallium, aluminum and zinc, sufficient corrosion resistance can be obtained. Moreover, these alloys can be age-hardened by aging at the intraoral temperature (37° C.) and Vickers hardness increases up to 300–320. Such a property can never be seen in a conventional dental gold alloy. Therefore, the present invention is extremely useful in industry as an advantageous invention.

Since the alloy of the present invention becomes hard by leaving it at room temperature, it is necessary to adjust the occlusal condition of the patient and to set the restoration to teeth of the patient within 3–4 hours after the solution treatment. If the alloy is hardened by leaving it at room temperature for a long period, it can be softened and used by applying the solution treatment again. This is also an advantageous point of the alloy.

In case that the alloy should be kept in the soft condition for a long time after the solution treatment, the alloy should be kept in a refrigerator or in a freezer so as to be immediately useable. This is also advantageous.

Although the invention has been described with a certain degree of particularly, it is understood that the present disclosure has been made only by way of example and that numerous changes in details of construction and the combination and arrangement of parts may be resorted to without departing from the scope of the invention as hereinafter claimed.

What is claimed is:

1. A dental gold alloy which is soft enough for adjustment of a patient's occlusal condition, which is age-hardenable with passage of time at temperatures encountered within a patient's oral cavity, and which has a single phase structure which imparts improved corrosion resistance, the dental gold alloy consisting essentially of:

82–67% by weight of gold;
   18–33% by weight of copper; and
   2–at % of an age-hardening accelerator which is at least one metal selected from the group consisting of gallium, and zinc,
   wherein the dental gold alloy has been subjected to a solution treatment by heating at 650–700° C. and quenching into water.

2. A dental gold alloy which is soft enough for adjustment of a patient's occlusal condition, which is age-hardenable with passage of time at temperatures encountered within a patient's oral cavity, and which has a single phase structure which imparts improved corrosion resistance, the dental gold alloy consisting essentially of:

82–67% by weight of gold;
   18–33% by weight of copper; and
   2–8 at % in total of an age-hardening accelerator which is at least one metal selected from the group consisting of 1–4% by weight of gallium, 0.4–2% by weight of aluminum and 1–5% by weight of zinc,
   wherein the dental gold alloy has been subjected to a solution treatment by heating at 650–700° C. and quenching into water without an subsequent extraoral hardening heat treatment.

3. The dental gold alloy according to claim 1, wherein the age-hardening accelerator is 1–4% by weight of gallium.

4. The dental gold alloy according to claim 1, wherein the age-hardening accelerator is 1–5% by weight of zinc.

* * * * *